US008224585B2

(12) United States Patent
Hoffman

(10) Patent No.: US 8,224,585 B2
(45) Date of Patent: *Jul. 17, 2012

(54) DOCUMENTING AND PRESENTING MUTATION OBSERVATIONS

(75) Inventor: Mark A. Hoffman, Lees Summit, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/962,205

(22) Filed: Dec. 7, 2010

(65) Prior Publication Data

US 2011/0179063 A1    Jul. 21, 2011

Related U.S. Application Data

(63) Continuation of application No. 10/679,900, filed on Oct. 6, 2003, now Pat. No. 7,869,956.

(51) Int. Cl.
*G06F 19/00* (2011.01)

(52) U.S. Cl. ............................................... 702/19

(58) Field of Classification Search ................. None
See application file for complete search history.

(56) References Cited

OTHER PUBLICATIONS den Dunnen, "Nomenclature for the description of sequence variations," Human Genome Variation Society, modified Dec. 7, 2003, 2 pp.

"Defining Sequence Analysis," DNA DNASTAR, Inc., 2003, 2 pp.
Cotton et al., "Quality Control in the Discovery, Reporting, and Recording of Genomic Variation," Human Mutation, vol. 15:16-21, 2000, 6 pp.
den Dunnen et al., "Mutation Nomenclature Extensions and Suggestions to Describe Complex Mutations: A Discussion," Human Mutation, vol. 15:7-12, 2000, 6 pp.
Beroud et al., "The UMD-p53 Database: New Mutations and Analysis Tools," Human Mutation, vol. 21:176-181, 2003, 6 pp.
Scriver et al., "Guidelines and Recommendations for Content, Structure, and Deployment of Mutation Databases," Human Mutation, vol. 13:344-350, 1999, 7 pp.
Claustres et al., "Time for a Unified System of Mutation Description and Reporting: A Review of Locus-Specific Mutation Databases," CSH Press, Genome Research, 2002, vol. 12: 680-688, 10 pp.

*Primary Examiner* — Lori A Clow
(74) *Attorney, Agent, or Firm* — Shook, Hardy & Bacon L.L.P.

(57) ABSTRACT

A method and system in a computing environment for documenting mutation observations is provided. The method includes receiving mutation information, disassembling the mutation information into discrete elements and storing the discrete elements. A method and system for presenting mutations is also provided. The method includes obtaining discrete elements for a mutation, obtaining a standard for presenting the mutation and assembling the mutation presentation utilizing the discrete elements and the standard of presentation.

20 Claims, 5 Drawing Sheets

DOCUMENTING AND PRESENTING MUTATION OBSERVATIONS

CROSS-REFERENCE TO RELATED APPLICATIONS

This application is a continuation of and claims priority from U.S. application Ser. No. 10/679,900, filed Oct. 6, 2003, now U.S. Pat. No. 7,869,956, and entitled "Computerized System and Method for Documenting and Presenting Mutation Observations. Application Ser. No. 10/679,900 is incorporated by reference in its entirety.

TECHNICAL FIELD

The present invention relates generally to the field of computer software. More particularly, the invention relates to a computerized system and method for documenting and presenting mutation observations.

BACKGROUND OF THE INVENTION

In recent years, genetic information has become increasingly available through research efforts such as this Human Genome Project. Currently, there are clinical diagnostic tests for more than 900 genes. Each gene may have multiple identified mutations. As the results of the Human Genome Project are used to identify additional genes involved in disease or clinical response, the number of clinically relevant gene targets for diagnostic testing will increase significantly. Furthermore, the increasing use of DNA sequencing as a diagnostic tool will lead to identification of more mutations.

The Human Genome Association (HUGO) has published a standard approach for describing DNA mutations. However, this standard has not been widely adopted. Many clinicians and researchers use approaches to describe mutations that differ from this published standard. Their approach is considered a user-preferred standard and has meaning within their group but differs from the published standard of HUGO.

While there are known programs that document mutation results, these programs do not store templates describing one or more standards nor do these programs use templates to store and present discrete values captured during the documentation of mutation observations.

Accordingly, there is a need for a system and method for documenting mutation observation and mutation results so the observations and results can be presented using published standards or user-preferred standards. There is also a need for a system and method of documenting mutations that flexibly and efficient exchanges and aggregates mutation data.

SUMMARY OF THE INVENTION

In one aspect of the present invention, a method and system in a computing environment for documenting mutation observations is provided. The method receives mutation information and disassembles the mutation information into discrete elements. The method then stores the discrete elements. The discrete elements of the mutation may be stored such that the elements can be used to present the mutation using both user-preferred and published standards.

In another aspect of the present invention, a method and system in a computing environment for presenting mutations is provided. The method obtains discrete elements of a mutation and obtains a standard for presenting the mutation information. The method assembles the mutation presentation utilizing the discrete elements and the standard of presentation. The standards may be user-preferred standards or published standards.

BRIEF DESCRIPTION OF THE SEVERAL VIEWS OF THE DRAWINGS

The present invention is described in detail below with reference to the attached drawing figures, wherein.

DETAILED DESCRIPTION OF THE INVENTION

Figure 1:
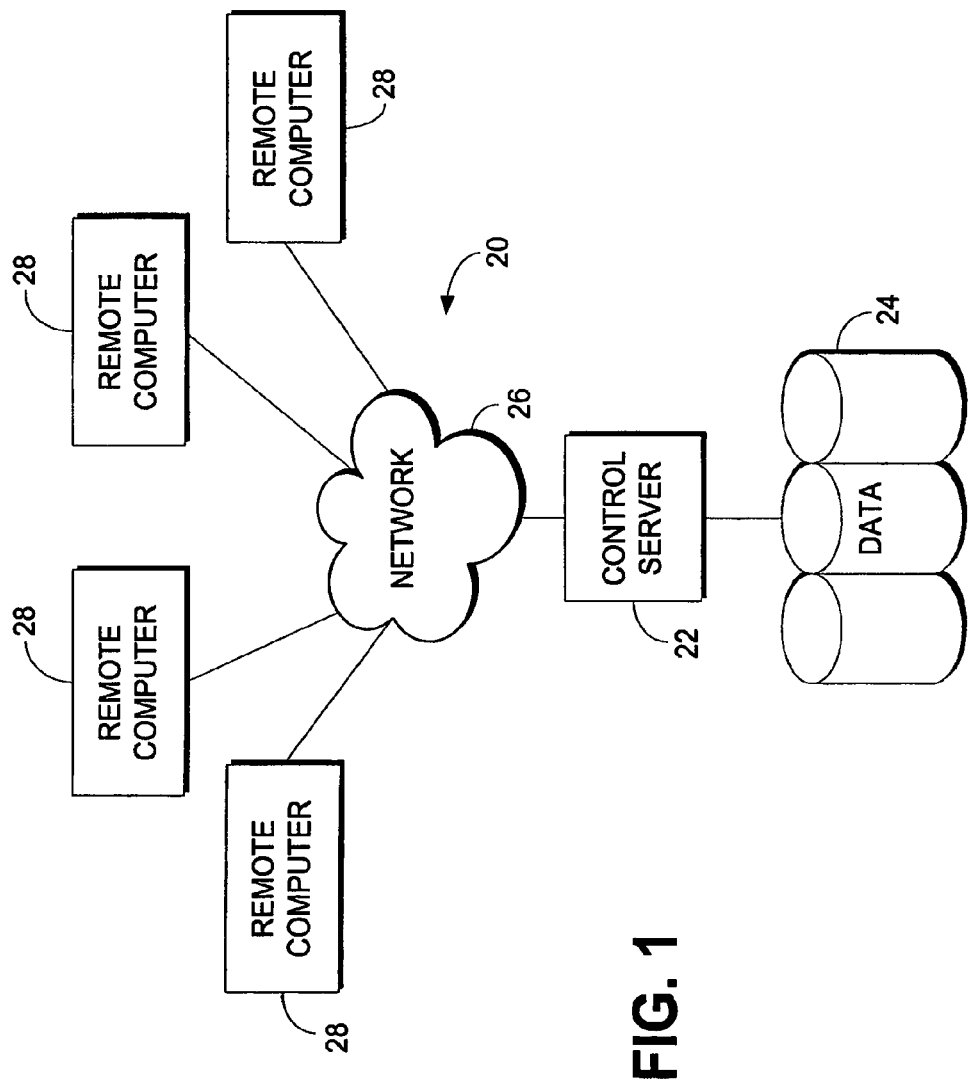
FIG. 1 is a block diagram of a computing system in accordance with an embodiment of the present invention.

The present invention provides a method and system for documenting and representing mutation observations using one or more standard notations. FIG. 1 illustrates an example of a computing system environment 20 on which the invention may be implemented. The medical information computing system environment 20 is only one example of a suitable computing environment and is not intended to suggest any limitation as to the scope of use or functionality of the invention. Neither should the computing environment 20 be interpreted as having any dependency or requirement relating to any one or combination of components illustrated in the exemplary environment 20.

The invention is operational with numerous other general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, network PCs, minicomputers, mainframe computers, distributed computing environments that include any of the above systems or devices, and the like.

The invention may be described in the general context of computer-executable instructions, such as program modules, being executed by a computer. Generally, program modules include, but are not limited to, routines, programs, objects, components, data structures that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 1, an exemplary system for implementing the invention includes a general purpose computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and nonremovable media. By way of example, and not limitation, computer readable media may comprise computer storage media and communication media. Computer storage media includes both volatile and nonvolatile, removable and nonremovable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical environment and/or a laboratory setting, for example, but not limited to, hospitals, other inpatient settings, a clinician's office, ambulatory settings, diagnostic labs, research laboratories, research facilities, and a patient's home environment. Clinicians include, but are not limited to, the treating physician, researchers, geneticists, laboratory technicians, specialists such as surgeons, radiologists and cardiologists, laboratory technicians, researchers, physician's assistants, nurse practitioners, nurses, nurse's aides, pharmacists, microbiologists, and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

As contemplated by the language above, the method and system of the present invention may be implemented on a stand-alone desktop, personal computer or any other computing device used in a medical environment, solitary research lab or any of a number of other locations.

Figure 2:
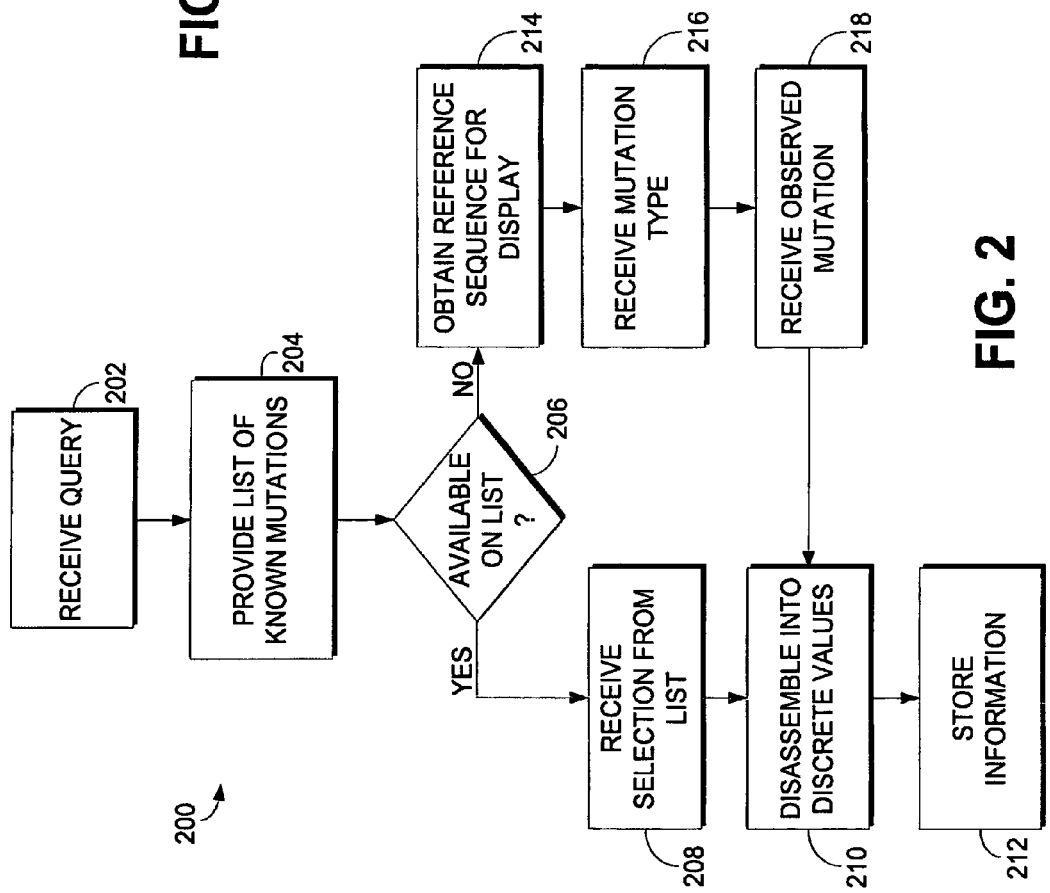
FIG. 2 is a flow chart representative of a computer program for documenting mutations in accordance with an embodiment of the present invention.

With reference to FIG. 2, a method 200 for documenting mutations is provided. Mutations may be documented for any organism. For example, mutations may be documented for humans, animals, vertebrates, invertebrates, plants, viruses, bacteria, fungi, prokaryotes, eukaryotes, and protista. A user seeks to document a particular mutation. The mutation to be documented may be obtained in any number of ways. In one embodiment, the mutation information is obtained from genetic testing. In another embodiment, the mutation to be documented is selected from a list of reference content in the database. A mutation, as used herein, is a permanent and heritable change to a DNA, which may also be represented in terms of the effects that a given mutation has on an RNA or protein molecule. DNA sequences may vary among individuals. These differences are called mutations and are the result of changes in the native genetic sequence due to substitutions, insertions, deletions, inversions, duplications, translocations and complex rearrangements.

At block 202, the system receives a query for a particular genetic information sequence. The query may be made by the user or initiated by the system in response to a clinical event or any of a number of events or activities. At block 204, the system provides a list of known mutations for the particular genetic information sequence. The list of mutations provided by the system may be for any genetic sequence, including, but not limited to, genes, proteins, and any known DNA and RNA sequences. There may be numerous known mutations for any particular gene, protein or sequence. For example, the sequence of nucleotides for a particular gene may vary between individuals.

The list of known mutations is displayed using a user interface. The user interface window presents a graphical user interface of the conventional kind for selecting a mutation from a comprehensive list. The list may include the common name for the mutation or any of a number of other formats that identify the mutation. These mutations may be presented in terms of the DNA alteration or in terms of the effects of the mutation on the RNA or protein sequence.

At block 206, if the mutation to be documented is available on the list of known mutations, the mutation is selected from the list. The selection is received at block 208. The mutation may be selected from the list of mutations displayed on the user interface in a variety of ways using any of a number of input devices and techniques.

If the mutation to be documented is not available in the list of known mutations at block 206, then the system obtains and displays the reference sequence for the particular genetic sequence at block 214. For example, if the sequenced genetic information is a gene, the ordered sequence of the nucleotides of the gene is displayed. If the genetic information is a protein sequence, the ordered sequences of the amino acids of the protein may be displayed. In one embodiment, the reference sequence is displayed using a sequence editor. From the sequence editor, a user can quickly and easily document mutations that are not presented on the list of known mutations. The mutation type is received at block 216 preferably from the user's selection. Types of mutations that may be documented, include, but are not limited to: substitutions, insertions, deletions, inversions, duplications, translocations and complex rearrangements.

At block 218, the observed mutation value is received preferably in response to the user's input. The sequence in the sequence editor may be dynamically modified to input the mutation information using the sequence editor. For example, a user may make edits such as, additions, deletions, and modifications, relative to the reference sequence in the sequence editor. The system may then disassemble the mutation information into discrete elements directly from the sequence editor and/or dynamically display the edits as entries in data entry fields. Mutation information may also be directly entered into the data entry fields. For example, if the mutation is a substitution, the system provides data entry fields for the user to enter the position of the substitution relative to the reference sequence, a data entry field for the native value of the genetic sequence and a data entry field for the observed value of the substitution. If the mutation is an insertion, the system provides data entry fields for the starting position of the insertion relative to the reference sequence, the length of the insertion and the specific sequence being inserted into the reference sequence. If the mutation is a deletion, the system provides data entry fields for the entry of the starting position of the deletion within the reference sequence and the ending position of the deletion within the reference sequence. For inversions, the system provides data entry fields including the starting position of the inversion within the reference sequence and the ending position of the inversion within the reference sequence. Additional fields and types of fields may be used to capture mutation information.

At block 210, the system disassembles the mutation into discrete elements. The discrete elements of the mutation are stored at block 212. By way of example, Table 1 illustrates the type and structure of data stored at block. The elements may be stored in a relational database, in an extensible markup language (XML) format or any of a number of other manners.

TABLE 1

| ID | Molecule Type | Genetic Sequence | Type | Start | Length | End | Ref Seq | Native Value | Observed |
|---|---|---|---|---|---|---|---|---|---|
| 1 | cDNA | CFTR | Sub | 3978 | | 3978 | NM_000492 | G | A |
| 2 | cDNA | CFTR | Sub | 15 | | 15 | NM_000492 | A | C |
| 3 | cDNA | HADHA | Ins | 2162 | 1 | | NM_000182 | — | C |
| 4 | cDNA | ACADM | Del | 1293 | 4 | 1296 | NM_000016 | TTAT | — |

The discrete elements may also include the molecule type such as genomic DNA, cDNA, RNA or a protein. Genomic DNA and all other DNA is composed of nucleotides in a specific order. The nucleotides that make DNA include adenine (A), guanine (G), cytosine (C) and thymine (T). The ordered sequence of nucleotides at a specific location in the genome which encodes a functional product, either protein or RNA, is a gene A protein is a large molecule composed of amino acids in a specific order. There are twenty naturally occurring amino acids that can be used to make a protein. The order of the amino acids is determined by the base sequence of the nucleotides of the gene coding for the protein.

RNA molecules are composed of strands of nucleotides much like genomic DNA. However, the nucleotides that makeup RNA include adenine (A), guanine (G), cytosine (C) and uracil (U). There are several classes of ribonucleic acids (RNA) including messenger RNA (mRNA), transfer RNA (tRNA), ribosomal RNA and other RNAs serving a different purpose.

Complementary DNA (cDNA) is DNA that has synthesized from a messenger RNA template corresponding to expressed sequences of genomic DNA. Complementary DNA is also composed of multiple nucleotides, A, T, C and G, in a specific order but lacks the intronic sequences found in genomic DNA.

The discrete elements also include the type of mutation (Type) such as a substitution (Sub), insertion (Ins), deletion (Del), inversion (Inv), duplication, translocation and complex rearrangement and the particular sequenced genetic information for which the mutation is to be documented. For example, when a user selects a mutation from a predefined list of mutations, the discrete information can be managed as reference content through association with a concept identifier with attributes that define the type, start, length, end and reference sequence ID.

Other discrete elements include a unique mutation identification value identifying the mutation (ID), a reference sequence identification value identifying the reference sequence (e.g. Gene Bank ID number), an identification value for identifying the individual being tested, the starting position of the mutation within the reference sequence, the ending position within the reference sequence, the length of an insertion, the native value of the sequenced genetic information, and the observed value of the mutation being documented. For example, in Table 1, a substitution mutation for cDNA is documented for the particular genetic sequence for the CFTR gene. The identification value for the reference sequence is 3978 NM_000492 and the mutation identification value is "1". The starting position for the substitution within the reference sequence is 3978 and the ending position is also 3978. The native value for the CFTR gene at the 3978 position is "G". The observed value of the nucleotide at the 3978 position of the substitution mutation is "T". A variety of other discrete values relating to the mutation may also be documented as needed.

Figure 3:
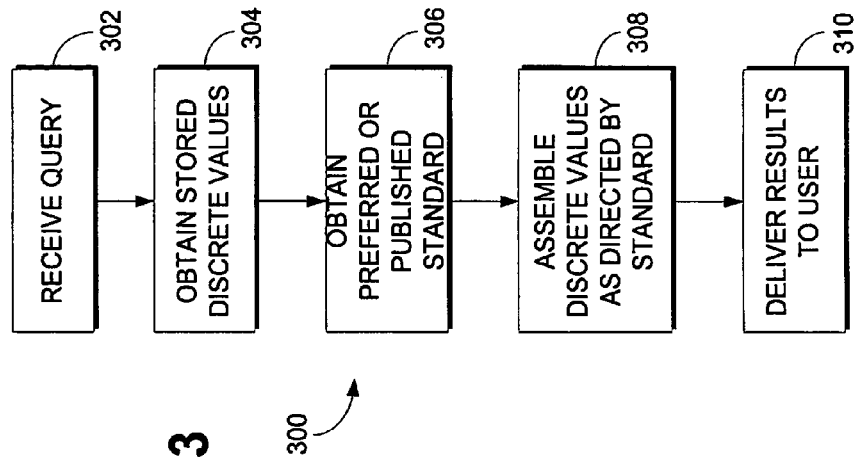
FIG. 3 is a flow chart representative of a computer program for presenting mutations in accordance with an embodiment of the present invention.

With reference to FIG. 3, a method 300 of providing mutation observations using preferred or published standards is shown. The system receives a query for a mutation presentation at block 302. At block 304, the system obtains the stored discrete values for the mutation.

At block 306, the system obtains the user-preferred standard or published standard for presenting the mutation. In one embodiment, the published standards and preferred standards are obtained from a relational database (or other storage type) containing the information in Table 2 below. The exemplary database contains the preferred standards for more than one user. Table 2 contains information regarding published and preferred standards for presenting a substitution mutation.

TABLE 2

| User | Position 1 | Position 2 | Position 3 | Position 4 |
|---|---|---|---|---|
| Published Standard | RefSeq Position | Normal value | Link symbol | Observed value |
| User 1 | Normal value | RefSeq Position | Observed Value | |
| User 2 | RefSeq Position | Observed Value | | |

In Table 2, the published standards for presenting a substitution mutation provide information about the mutation in four positions. Position 1 is the position within the reference sequence (RefSeq Position) at which the substitution value occurs. Position 2 is the native value (e.g. nucleotide(s) or amino acid(s)) of the sequenced genetic information. Position 3 is a link symbol such as ">" and Position 4 is the observed value (e.g. nucleotide(s) or amino acid(s)) of the mutation. However, the preferred standards for viewing a mutation for User 1 provide information regarding the mutation only in three positions. Position 1 is the native value (e.g. nucleotide(s) or amino acid(s)) of the sequenced genetic information. Position 2 is the position within the reference sequence of the substitution and Position 3 is the observed value of the mutation (e.g. nucleotide(s) or amino acid(s)).

Notably, the information regarding published and preferred standards may be obtained from any number of sources. Further, the published and preferred standards may be stored in different databases and formats.

At block 308, the system assembles the mutation presentation by using the discrete values as directed by the preferred or published standard. At block 310, the system delivers the mutation presentation.

Figure 4:
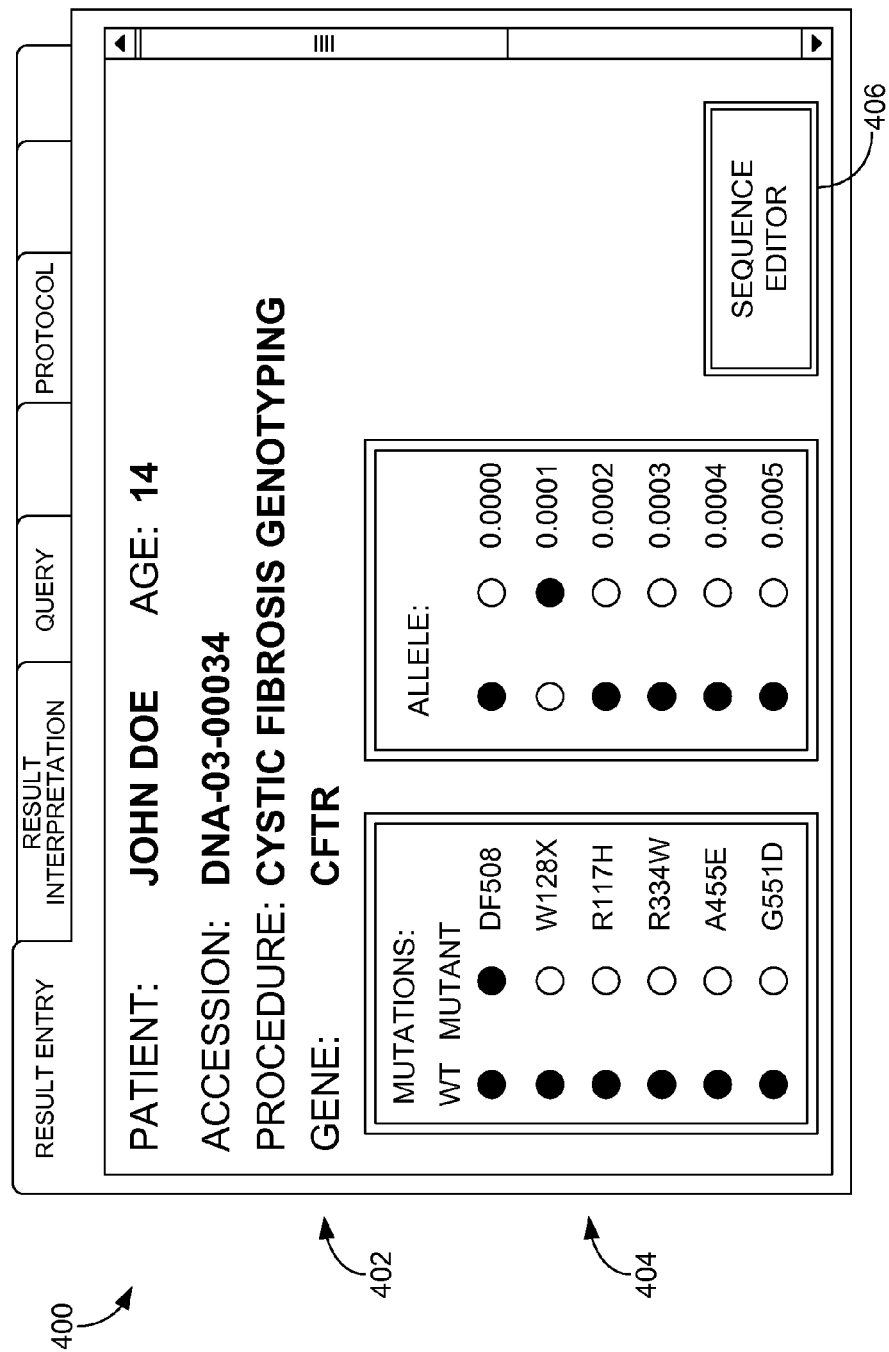
FIG. 4 is a screen shot illustrating an exemplary implementation of documenting DNA mutations in accordance with an embodiment of the present invention.

With reference to FIG. 2, by way of an example to demonstrate the operation of the present invention, documentation of a Cystic Fibrosis genetic test result for patient John Doe is demonstrated. First, at block 202, the system is queried for known mutations for Cystic Fibrosis. The genetic results indicate that the patient has a deletion of nucleotides 1652-1655 in the Cystic Fibrosis gene which results in the deletion of phenalanine (F) at position 508 of the protein sequence (D F508). The system is configured to present this and other mutations in terms of the resulting amino acid substitutions. With reference to FIG. 4, a screen shot 400 of a list of current mutations 404 for the Cystic Fibrosis gene 402 is shown. The DF508 mutation is listed. The user selects the DF508 mutation to be documented. With reference back to FIG. 2, the system receives the user's selection of the known mutation (DF508) from the list at block 208. The system disassembles the DF508 results into discrete values at block 210, and, at block 212, stores this information.

With reference to FIG. 3, later, if the clinician wants to view the mutation using the preferred standards of the presentation, the system receives the query for the mutation at block 302. At block 304, the system obtains the stored discrete values and at block 306 the system obtains the user's preferred standards. At block 308, the system assembles the discrete values as directed by the preference. At block 310, the system delivers the mutation presentation to the user. The user's preferred standards for presentation of a substitution mutation are: type of mutation, Native Value; Location within the Reference Sequence; Observed Value or lack of observed value. In this instance, the preferred presentation of the DF508 mutation del 1652-1655 would be "del F508".

However, in this example, a researcher also wants to extract CFTR mutation results from the system and aggregate those results with those of other researchers. Further, in this example, the researcher wants to transfer the results using published standards rather than clinician's preferred standards. At block 302, the system receives the query for CFTR mutations and at block 304 obtains the stored discrete values for each CFTR mutation. At block 306, the system obtains the published standards and assembles the discrete values as directed by the published standards for presentation. At block 310, the system delivers the mutation presentation. According to current published standards for presentation of a deletion mutation are: Location within Reference Sequence; "del"; positions deleted. In this example, the presentation of the DF508 mutation according to published standards would be "1652delGTC".

In operation, by way of another example, a clinician receives a different Cystic Fibrosis genetic test result for patient John Doe to be documented. The sequenced genetic results indicate that the patient has a previously unknown mutation of the Cystic Fibrosis gene. With reference to FIG. 4, a screen shot 400 of list of mutations 404 for the Cystic Fibrosis gene 402 is shown. The unknown mutation is not in the list of known mutations. As such, the user selects sequence editor 406 to document the mutation. After receiving the selection of the sequence editor 406, the system obtains and displays the reference sequence of the CFTR gene.

Figure 5:
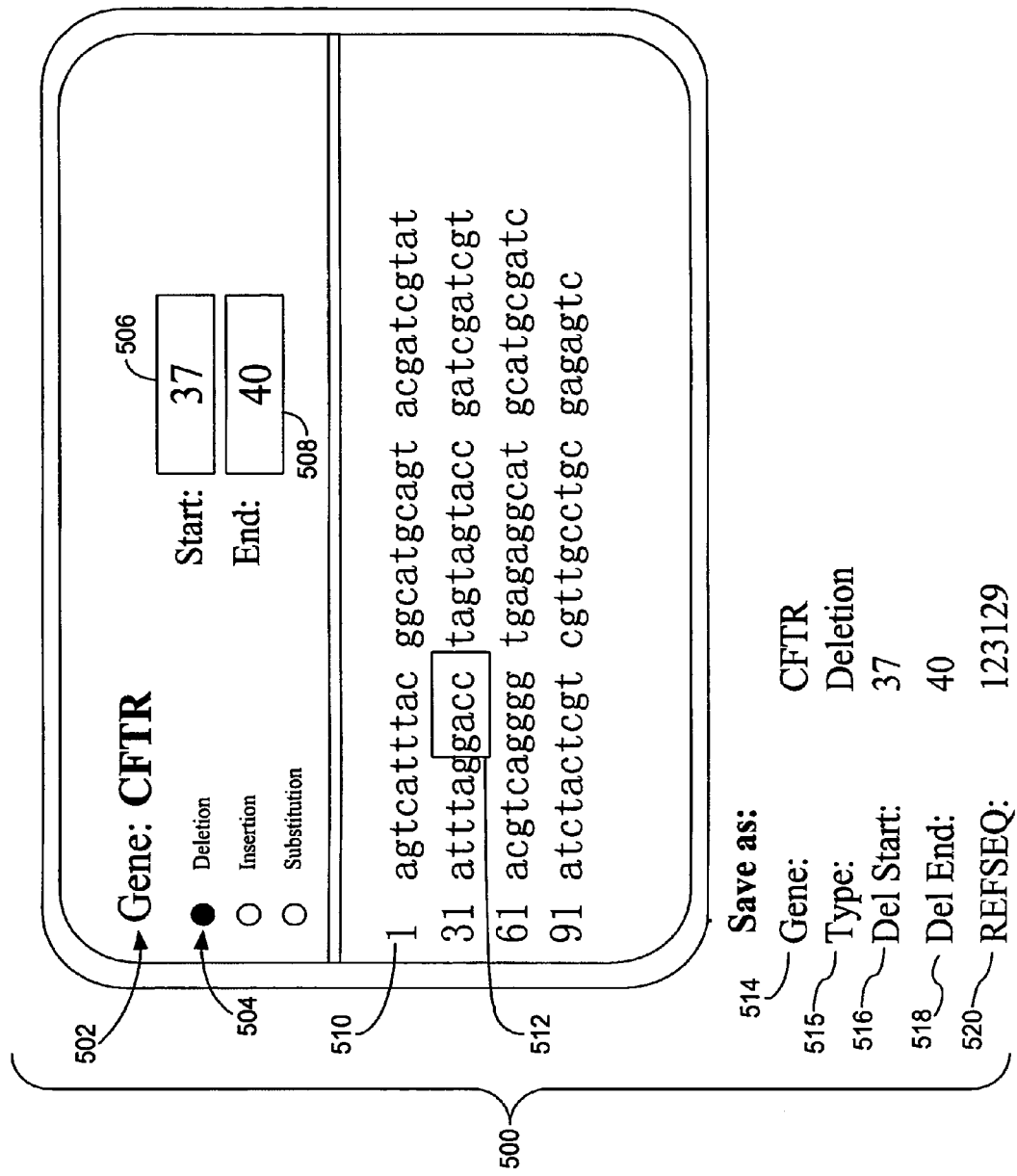
FIG. 5 is a screen shot illustrating an exemplary implementation of documenting DNA mutations, for example, a reference sequence having SEQ ID NO:1, in accordance with an embodiment of the present invention.

With reference to FIG. 5, a screen shot 500 displays reference sequence 510 and data entry fields 506 for a hypothetical deletion mutation 504. The user enters the starting position of the deletion within the reference sequence in data entry field 506 and the ending position of the deletion within the reference in data entry field. Alternatively, this information may also be entered directly into the sequence editor. For example, nucleotides "GACC" 512 from position 37 to position 40 are deleted relative to the reference sequence contained in the sequence editor. The system could utilize these edits from the sequence editor automatically or may also dynamically display the edits as data in the data entry fields 504, 506 and 508. In this example, the system stores the discrete values as the CFTR gene 514, the type of mutation 515, the starting position of the deletion 516 within the reference sequence, the ending position 518 of the deletion within the reference sequence and an identification value identifying the reference sequence 520.

In operation by way of yet another example, a clinician receives a Cystic Fibrosis genetic test result for patient John Doe. The sequenced genetic result indicates that the patient has an unknown mutation of the Cystic Fibrosis gene. With reference to FIG. 4, a screen shot 400 of list of mutations 404 for the Cystic Fibrosis gene 402 is shown. The unknown mutation is not on the list of known mutations. As such, the user selects sequence editor 406 to document the mutation. After selecting the sequence editor 406, the system obtains and displays the reference sequence of the CFTR gene.

Figure 6:
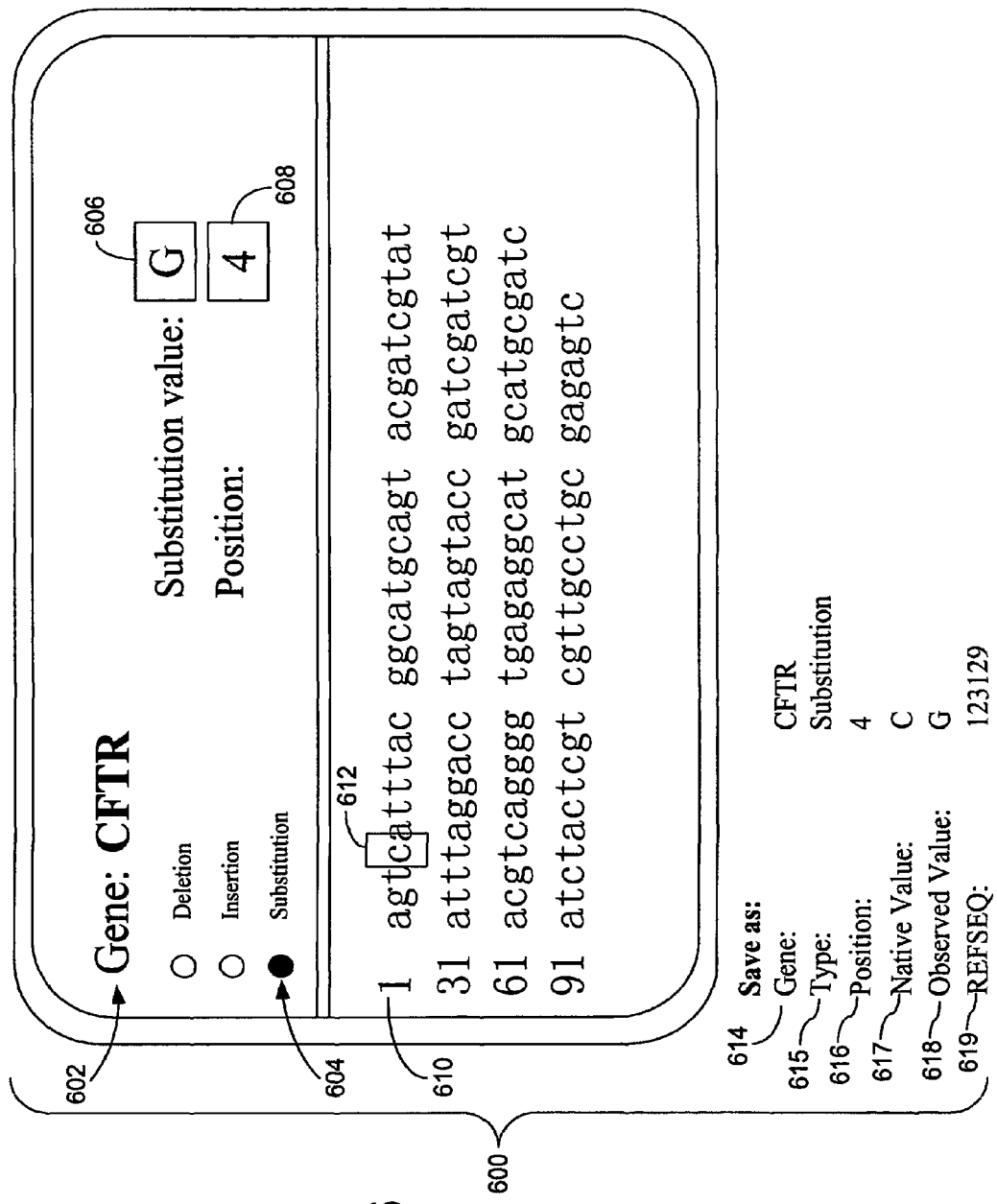
FIG. 6 is a screen shot illustrating an exemplary implementation of documenting DNA mutations, for example, a reference sequence having SEQ ID NO:1, in accordance with an embodiment of the present invention.

With reference to FIG. 6, a screen shot 600 displaying reference sequence 610 and data entry fields 606 and 608 for a substitution mutation 604 are shown. The user enters the substitution value "G" (e.g. observed nucleotide) into data entry field 606 and the position of the substitution "4" within the reference sequence in data entry field. As can be seen in the sequence editor, nucleotide "C" 612 at position "4" is substituted with the observed value "G." The system then stores the discrete values. For example, the system stores the discrete values as the CFTR Gene 614, the type of mutation 615, the position of the substitution 616, the native value 617, the observed value 618 and an identification value identifying the reference sequence 619.

The present invention provides a method and system for documenting mutation observations. The present invention also provides a method and system for presenting mutation observations. Although the invention has been described with reference to the preferred embodiment illustrated in the attached drawing figures, it is noted that substitutions may be made and equivalents employed herein without departing form the scope of the invention as recited in the claims. For example, additional steps may be added and steps omitted without departing from the scope of the invention.

The invention claimed is:

1. A method in a computing environment for facilitating a display of mutation information, the method comprising:
   receiving mutation information;
   disassembling the mutation information into discrete elements, wherein the discrete elements include a patient identification value, a reference sequence identification value, a starting point value within a reference sequence, and an ending point within the reference sequence;
   storing said discrete elements such that the mutation may be presented using both user-preferred and published standards;
   receiving a query from a user for a mutation presentation;
   receiving a selection from the user of one of the user-preferred and published standards;
   assembling, via a computing device, one or more of the discrete elements in response to the selection from the user of the one of the user-preferred and published standards, the one or more discrete elements being assembled in accordance with the selected user-preferred standard or published standard; and
   displaying the mutation to the user in accordance with the user-preferred standard or the published standard selected by the user.

2. The method of claim 1, wherein the mutation information is for one of a substitution, inversion, insertion, deletion, translocation, complex rearrangement and combinations thereof.

3. The method of claim 1, wherein the discrete elements include one or more of a mutation identification value, a mutation type, a length of an insertion, a native value of sequenced genetic information, and an observed value of the mutation.

4. The method of claim 1, wherein the user-preferred standards are user defined.

5. The method of claim 1, wherein the published standards are the recommended standards published by the Human Genome Association.

6. The method of claim 1, wherein the published standards are the standards adopted by the genetics community comprising genetic clinicians.

7. The method of claim 1, further comprising:
   providing a list of known mutations for particular sequenced genetic information.

8. The method of claim 7, wherein the sequenced genetic information is one of a gene, a protein, sequenced DNA other than a gene and sequenced RNA.

---

SEQUENCE LISTING

<160> NUMBER OF SEQ ID NOS: 1

<210> SEQ ID NO 1
<211> LENGTH: 117
<212> TYPE: DNA
<213> ORGANISM: Artificial
<220> FEATURE:
<223> OTHER INFORMATION: Artificial Sequence for Exemplary Purposes

<400> SEQUENCE: 1
agtcatttac ggcatgcagt acgatcgtat atttaggacc tagtagtacc gatcgatcgt      60
acgtcagggg tgagaggcat gcatgcgatc atctactcgt cgttgcctgc gagagtc       117

9. The method of claim 8, further comprising:
receiving a selection of a mutation from the list of known mutations.

10. The method of claim 1, wherein the mutation information is for one of humans, animals, vertebrates, invertebrates, plants, viruses, bacteria, fungi, prokaryotes, eukaryotes, and protista.

11. The method of claim 10, wherein the mutation information is for a particular patient.

12. One or more non-transitory computer-readable storage media having computer-executable instructions embodied thereon that, when executed, perform a method for facilitating a display of mutation information, the method comprising:
obtaining discrete elements for mutation information, wherein the discrete elements include a patient identification value, a reference sequence identification value, a starting point value within a reference sequence, and an ending point within the reference sequence;
obtaining a standard for presenting the mutation information, the standard being selected by a user from among a set of user-preferred and published standards;
assembling the mutation information utilizing the discrete elements in response to the standard selected by the user from among the set of user-preferred and published standards, the mutation information being assembled in accordance with the selected standard of presentation; and
displaying the mutation to the user in accordance with the standard of presentation selected by the user, wherein
(1) when the user selects a user-preferred standard, the mutation information is assembled and displayed in accordance with the user-preferred standard, and
(2) when the user selects a published standard, the mutation information is assembled and displayed in accordance with the published standard.

13. The media of claim 12, wherein the user-preferred standard is user defined.

14. The media of claim 12, wherein the published standard is published by the Human Genome Association.

15. A method in a computing environment for facilitating a display of mutation information, the method comprising:
receiving a selection from a user of a standard for presenting mutation information, the standard being selected from among a set of user-preferred and published standards;
obtaining discrete elements for the mutation information, wherein the discrete elements include a reference sequence identification value; and
in response to the standard selected by the user from among the set of user-preferred and published standards, using the discrete elements to assemble the mutation information, via a computing device, in accordance with the selected user-preferred or published standard of presentation.

16. The method of claim 15 further comprising displaying the mutation to the user in accordance with the standard of presentation selected by the user, wherein when the user selects a user-preferred standard, the mutation information is assembled and displayed in accordance with the user-preferred standard, and when the user selects a published standard, the mutation information is assembled and displayed in accordance with the published standard.

17. The method of claim 15, wherein the user-preferred standard is user defined.

18. The method of claim 15, wherein the published standard is published by the Human Genome Association.

19. The method of claim 15, wherein the discrete elements include one or more of a mutation identification value, a patient identification value, a mutation type, a starting point value with the reference sequence, an ending point with the reference sequence, a length of an insertion, a native value of sequenced genetic information, and an observed value of the mutation.

20. The method of claim 15, wherein the mutation information is for one of humans, animals, vertebrates, invertebrates, plants, viruses, bacteria, fungi, prokaryotes, eukaryotes, and protista.

* * * * *